United States Patent
Meier et al.

(10) Patent No.: US 6,532,382 B2
(45) Date of Patent: Mar. 11, 2003

(54) METHOD FOR CALCULATING THE HEART RATE VARIABILITY FOR BEING APPLIED IN AN ECG MONITOR, AND ECG MONITOR COMPRISING AN APPROPRIATE CALCULATION PROGRAM

(75) Inventors: Jan H. Meier, Uttenreuth (DE); Eric Fournié, Erlangen (DE)

(73) Assignee: Biotronik Mess- und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 111 days.

(21) Appl. No.: 09/780,366

(22) Filed: Feb. 12, 2001

(65) Prior Publication Data

US 2001/0016694 A1 Aug. 23, 2001

(30) Foreign Application Priority Data

Feb. 11, 2000 (DE) .......................................... 100 06 154

(51) Int. Cl.[7] .............................................. A61B 5/0402
(52) U.S. Cl. ........................ 600/515; 509/521; 509/515
(58) Field of Search ................................. 128/897–898; 600/509, 512, 515, 516, 518, 519, 521

(56) References Cited

U.S. PATENT DOCUMENTS 5,772,604 A * 6/1998 Langberg et al. ........... 600/518

5,827,195 A * 10/1998 Lander ....................... 600/509

* cited by examiner

Primary Examiner—Kennedy Schaetzle
Assistant Examiner—Kristen L Droesch
(74) Attorney, Agent, or Firm—Browdy and Neimark, P.L.L.C.

(57) ABSTRACT

A method of calculating the heart rate variability of the human heart to be used in an ECG monitor comprises the following procedural steps:

scanning of the ECG signal received from the ECG monitor during a scanning interval, determining from the scanned ECG signals a number of discrete measuring values representative of the heart rate variability, and evaluating these measuring values on the basis of the Fourier transformation, wherein the frequency spectre of the measuring values is calculated from the Fourier coefficients of the Fourier transformation, which are for their turn calculated from a combination of said measuring values with the sinus- and cosinus-shaped Fourier vectors of the Fourier transformation wherein the Fourier vectors are involved in the calculation in the form of a number of discrete real numerical vector values, and replacing of the numerical vector values for calculating the frequency spectrumof the scanned measuring values by rough, integral approximate vector values of a limited number which roughly form the shape of the Fourier vectors.

10 Claims, 4 Drawing Sheets

METHOD FOR CALCULATING THE HEART RATE VARIABILITY FOR BEING APPLIED IN AN ECG MONITOR, AND ECG MONITOR COMPRISING AN APPROPRIATE CALCULATION PROGRAM

BACKGROUND OF THE INVENTION

1. Field of the Invention

The present invention relates to a method for calculating the heart rate variability of the human heart for implementation in an ECG monitor, and further to an ECG monitor having an operating program of which implements said calculation program. In this context, "ECG monitor" is to be understood as any external or implantable device which detects and evaluates ECG signals, that is, apart from actual monitors, also for instance, the respective functional components included in pacemakers and defibrillators.

2. Background Art

Regarding the background of the invention, it has to be stated that heart rate variability is a risk indicator in the clinical practice with regard to patients having suffered from a cardiac infarction. It is therefore a declared objective of cardiology to record and evaluate the heart rate variability of such post-infarction patients in order to be able to initiate appropriate measures in case of dangerous values.

Another aspect in the context of the present invention is the trend to design cardiological monitoring devices for patients suffering from heart diseases in a way so as to make the device implantable into the body of the patient. When determining the heart rate variability, the frequency spectrum of the heart rate is determined, and the ratios of the maximum values are evaluated. Usually, the frequency spectrum is analysed using the so-called "Fourier transformation" by scanning the ECG signal received by the ECG monitor during a specific scanning interval and determining from this signal a number of discrete measuring values representative of the heart rate variability, such as RR intervals.

As will be explained in greater detail in the description of the example embodiment with reference to the specific formulas, the frequency spectrum of the measuring values is calculated using the Fourier coefficients of the Fourier transformation. The Fourier coefficients themselves are calculated using a combination of the measuring values and the sinus- or cosinus-shaped Fourier vectors of the Fourier transformation. The problem of the usual Fourier transformation lies in the fact that for the mathematical implementation the (continuous) Fourier vectors have to be transformed into discrete support points. The support points are real figures reflecting the sinus- or cosinus-shaped course of the Fourier vectors. Depending upon the selected number of support points the number of multiplications required for calculating the Fourier coefficients from the Fourier vectors and the measuring values increases superproportionately. Therefore, the large number of multiplications using real figures requires an extreme calculating effort and an enormous need of memory capacity.

These high calculating and memory needs exceed by far the capacity of micro-processor systems available for implanted cardiological devices, thus rendering the application of a Fourier transformation for frequency analysis impossible as long as the prior art calculation methods and processor systems are used.

SUMMARY OF THE INVENTION

As a solution for these problems, the present invention suggests the replacement of the known (Fast) Fourier transformation in the analysis of the heart rate variability by an approximation method which, on the basis of the Fourier transformation, replaces the numerical vector values for calculating the frequency spectre of the scanned measuring values by a limited number of rough approximate vector values wherein these approximate vector values roughly reflect the course of the Fourier vectors. This method allows a considerable reduction of the calculating and memory needs and thus the application in implanted devices. The simplification is achieved by no longer presenting the Fourier vectors by support points of the sinus and cosinus functions in the form of real figures. Instead, said support points are selected as rough, integral approximate vector values, preferably based on the figures $-1$, $0$, and $+1$. A preferred upper limit for the number of approximate values may be five figure values $-2$, $-1$, $0$, $+1$, $+2$ symmetrically surrounding the value $0$. As a whole, this "roughening" of the support points generates a sort of "fuzzy Fourier transformation".

Suitable evaluation results have been obtained when the limit for transforming the real numerical vector values into the approximate values $-1$, $0$, and $+1$ was $+/-0.33$. A numerical vector value between $-0.33$ and $+0.33$ results in an approximate value of $0$ while numerical vector values $>+0.33$ or $<-0.33$ result in approximate values of $+1$ and $-1$, respectively. As in the conventional Fourier transformation the sum of the approximate vector values for each Fourier vector has a value of $0$, it is possible in case of a deviation of the sum of approximate vector values from the $0$ value to correct at least one approximate value to obtain a sum value of $0$. Thus, an ostensible offset in the analyzed frequency spectre and/or a wrong peak in the calculated frequency spectre at low frequencies are avoided.

The invention further relates to an EGG monitor comprising an operating program which implements the calculation method described above. Thus, said EGG monitor becomes implantable into the human body and/or can be integrated into a pacemaker.

Now, the calculation method according to the invention shall be explained in greater detail with respect to an example embodiment and with reference to the drawings attached hereto.

DESCRIPTION OF THE PREFERRED EMBODIMENT

Figure 1:
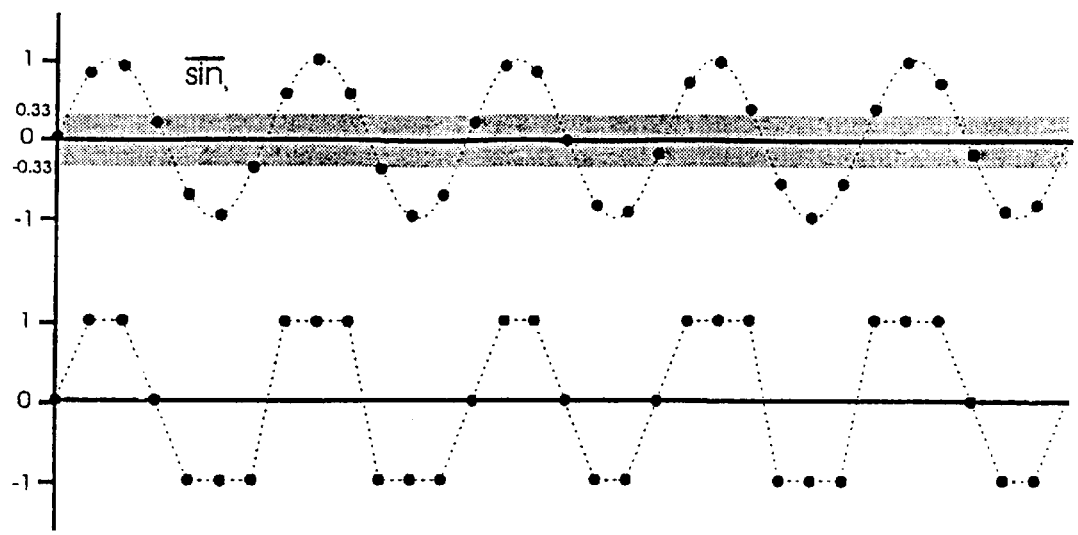
FIG. 1 shows a comparative diagram of the sinus vector of the Fourier transformation itself and its representation by integral approximate vector values.

For a better understanding of the invention, the calculation principle of the Fourier transformation shall be concisely recalled at the beginning of this description. The Fourier theorems say that a series of measuring values $R_i$ (i=0 ... 2N-1) can be described as $$R_i = 1/N \sum_{n=1}^{N-1} s_n \sin(\pi ni/N) + 1/N \sum_{m=0}^{N-1} c_m \cos(\pi mi/N) \quad (1)$$

The spectral components $s_n$ and $c_m$ are defined by $$s_n = \sum_{i=0}^{2N-1} R_i \sin(\pi ni/N) = \overline{R} \cdot \overline{\sin}_n \quad (2)$$

$$c_0 = 1/2 \sum_{j=0}^{2N-1} s_i$$

$$c_m = \sum_{j=0}^{2N-1} R_i \cos(\pi mj/N) = \overline{R} \cdot \overline{\cos}_n$$

Thus, the Fourier coefficients result from a linear combination of the measuring value vector $\overline{R}$ and the sinus- or cosinus-shaped Fourier vectors $\overline{\sin}_n$ or $\overline{\cos}_n$, respectively. These Fourier vectors $$\overline{\sin}_n=(0, \sin(\pi n/N), \sin(2\pi n/N)), \ldots, \sin((2N-1)\pi n/N)) \quad (3)$$

$$\overline{\cos}_n=(0, \cos(\pi n/N), \cos(2\pi n/N)), \ldots, \cos((2N-1)\pi n/N))$$

are the system's eigenvectors.

In case of a scanning interval of $\Delta t$ the following formula applies to the amplitude A of a frequency component f:

$$A(f=n/2N \Delta t) = \sqrt{(s_n^2 + c_n^2)} \quad (4)$$

If the above equation system were implemented by a control program in an ECG monitor, a value of N=16 in the equation system (2) would require 1024 multiplications for this discrete Fourier transformation. The eigenvectors at an 8-bit resolution and 32 eigenvectors comprising 32 components would require 1 kbyte of memory. This requirement make the use in an implanted device impossible.

The fuzzy Fourier transformation according to this invention shall now be explained with reference to FIG. 1. Using the formulas (3), the numerical vector values are replaced by rough integral approximate vector values, i.e. -1, 0, and +1. The assignment rule is as follows:

-0.33<numerical vector value<+0.33: approximate value=0 numerical vector value<-0.33: approximate value=-1 numerical vector value>+0.33: approximate value=+1

FIG. 1 shows this approximation for the magnitudes 2N=32, n=4. In the upper region, the sinus eigenvector is shown with the respective support points in the form of real numerical values. In accordance with the assignment rule mentioned above, this sinus eigenvector is transformed into the course shown in the lower region of FIG. 1. That is, the numerical vector values $\sin(\pi ni/N)$ and $\cos(\pi ni/N)$ of the equations (2) are replaced by -1, 0, or +1, respectively. Thus, no multiplications are required any more to calculate the magnitudes $s_n$, and $c_n$, but essentially only additions. Further, the components of the own vectors can be stored in the form of the approximate vector values in 2-bit resolution memories which reduces the memory need to one fourth compared with the example described above.

The aforementioned numerical approximate vector values for the fuzzy Fourier transformation may be stored in a table describing these trigonometric function approximations.

Alternatively, those points in which the function values are changed according to the assignment rule mentioned above can be calculated by a small mathematical effort. This means a kind of "online calculation" of the fuzzy Fourier support points which results in saving calculating capacity and power need compared with the storage of precalculated support points.

Thus, the following equation applies to the approximate value=+1:

$$\sin(\pi ni/N) \geq 0.33$$

$$\Rightarrow 0.3363 +/- 2\pi \leq \pi ni/N \leq 2.8053 +/- 2\pi$$

$$\Rightarrow 0.1070 N +/- 2N \leq \pi ni \leq 0.8930 N +/- 2N$$

The approximate value 0 applies to 0.8930 N+/-2N<ni<1.1070 N+/-2N

The approximate value -1 applies to 1.070 N+/-2N≦ni≦1.8930 N+/-2N.

Similarly the cosinus approximate values are calculated to obtain an approximate value=+1, if ni>0+/-2N and <0.393 N +/-2N or >1.6070 N +/-2N and <2N +/-2N, approximate value =-1, if ni ranges between 0.6070 N +/-2N and 1.3930 N +/-2N, and approximate value =0, if ni is beyond the above value ranges.

As a further simplification, the equation (4) may be replaced by $$A(f=n/2N\Delta t) \approx |s_n| + |c_n| \quad (5)$$

The fuzzy Fourier transformation basically described above was applied in a simulation test, and the respective spectral components $s_n$ and $c_n$ were calculated and compared with the discrete Fourier transformation using exact values. As an input signal $R_i$ the following signal was used which represented a sum of two sinus signals, one random signal and one offset:

$$R_i = C_1 \sin(\delta\phi_1 i + \phi'_1) + C_2 \sin(\delta\phi_2 i \phi'_2) + C_3 \text{Random}_i[-1, \ldots +1] + C_4$$

The amplitude coefficients $C_1$, $C_2$, $C_3$ and $C_4$ and the phase coefficients $\delta\phi_1$, $\phi'_1$, and $\phi'_2$ are freely selectable.

As a simulation test, a single sinus signal was calculated with $\delta\phi_1 = 5\pi/19$ and $\phi'_1 = \pi/4$. The amplitude coefficients $C_2$, $C_3$ and $C_4$ were set to 0.

Figure 2:
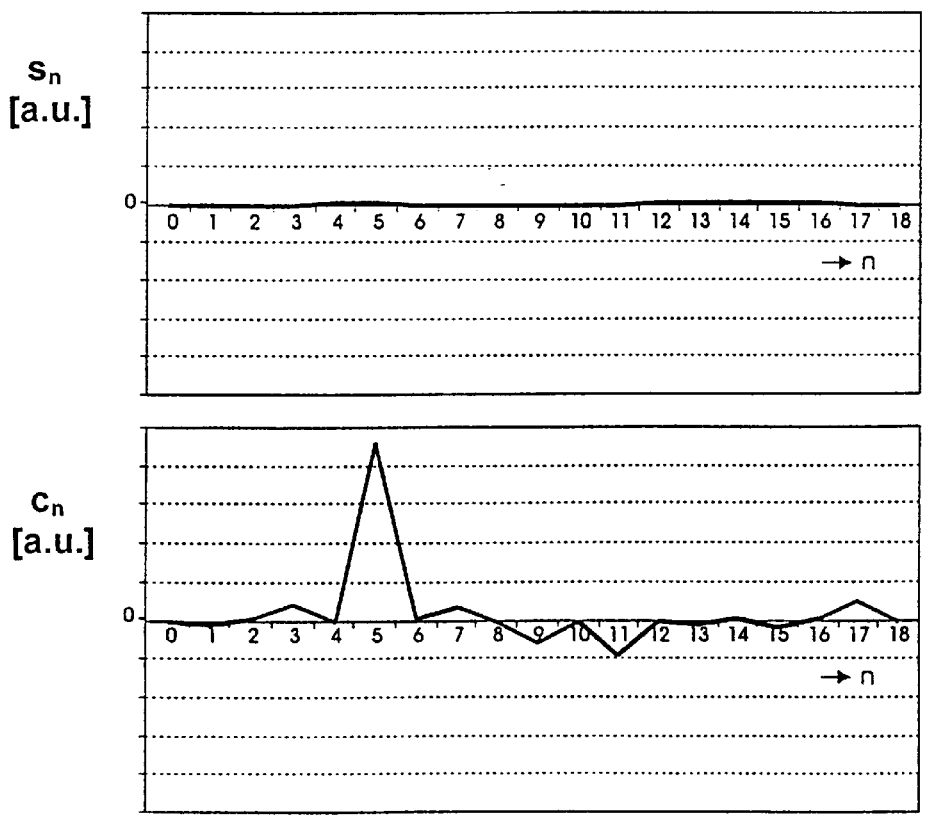
FIG. 2 shows a representation of the spectral components of a single sinus signal calculated using the fuzzy Fourier transformation approximation method.

The discrete Fourier transformation results in only one single discrete peak in the $c_n$ course at n=5 as the phase displacement of $\pi/4$ assumes a cosinus signal. In FIG. 2, this peak is not actually shown.

The application of the fuzzy Fourier transformation approximation method results in the courses of the spectral components $s_n$ and $c_n$ shown in FIG. 2. It is completely obvious that the approximation method also reproduces the peak at n=5 in the spectral component $c_n$, which provides an evidence for the correctness of the approximation method. However, the base lines of $s_n$ and $c_n$ do not constantly equal 0 but vary around this value. Up to 20% of the maximum amplitude value are reached, but this is tolerable.

The result of a more complex simulation using the input signal mentioned above is shown in FIG. 3. Here, a mix of two random sinus signals having the following parameters was used as basis:

$$C_1 = C_2 = 0.5 \; C_3; \; \delta\phi_1 = 5\pi/19; \; \phi'_1 = 0; \; \delta\phi_2 = 9\pi/19; \; \phi'_1 = \pi/4$$

Figure 3:
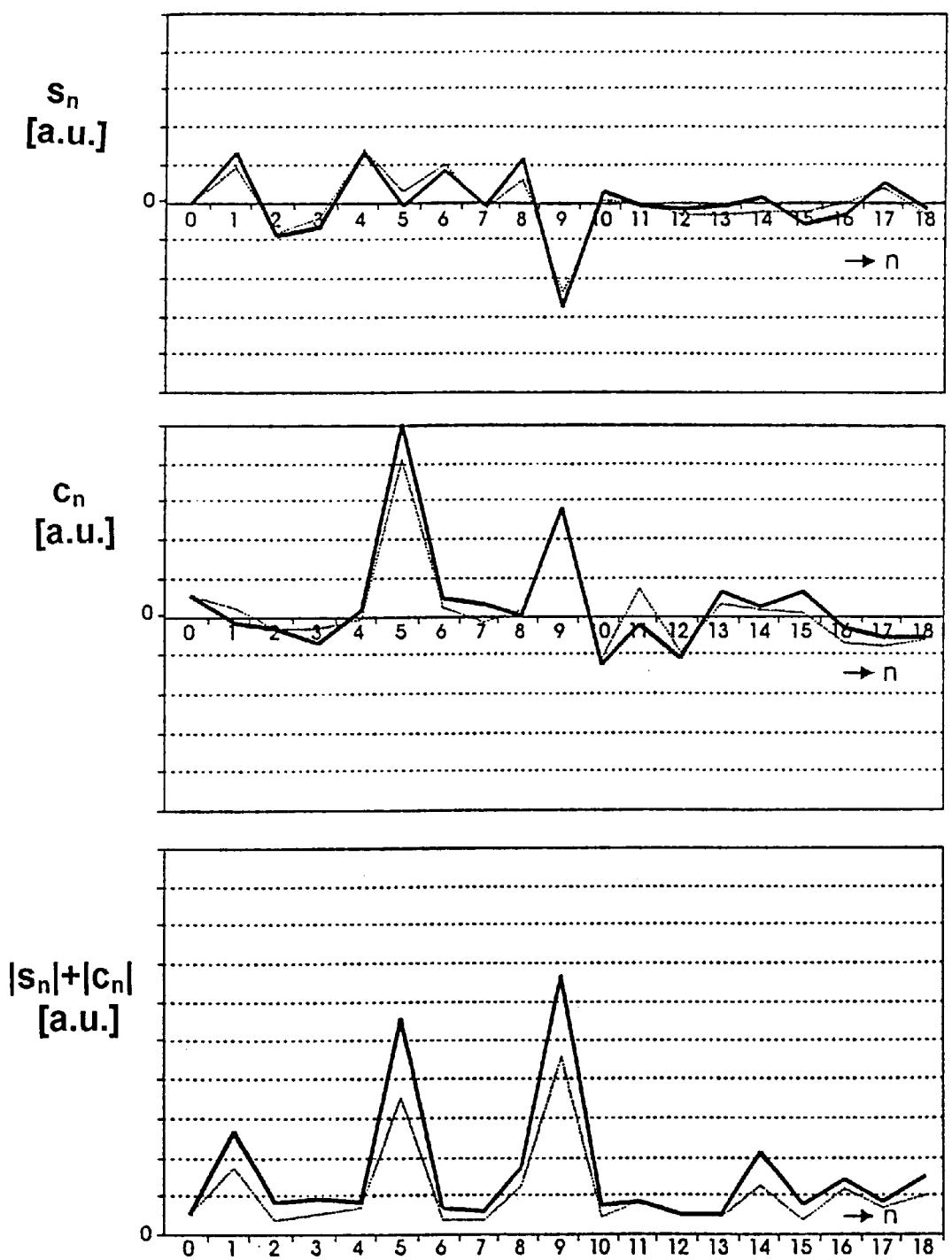
FIG. 3 shows a representation of the spectral components calculated in this manner and the frequency-depending amplitudes for a mix of two sinus signals and one random signal.

FIG. 3 shows the two spectral components $s_n$ and $c_n$ and the frequency-dependent amplitude A calculated using the formula (5). The results obtained by using the approximation method according to this invention are drawn as uninterrupted lines and the results obtained from the discrete Fourier transformation as dotted lines.

A comparison between the two signal courses in the various parts of the diagram shows that the results of the discrete and of the fuzzy Fourier transformation method are very similar which renders the approximation method useful. Only the base line of the frequency-dependent amplitude A(f) in the lowest part of FIG. 3 has been raised by the random portion. However, although the random signal is twice as large as the two sinus signals the existence of these two signals is visible in the frequency spectrum at n=5 and n=9.

Figure 4:
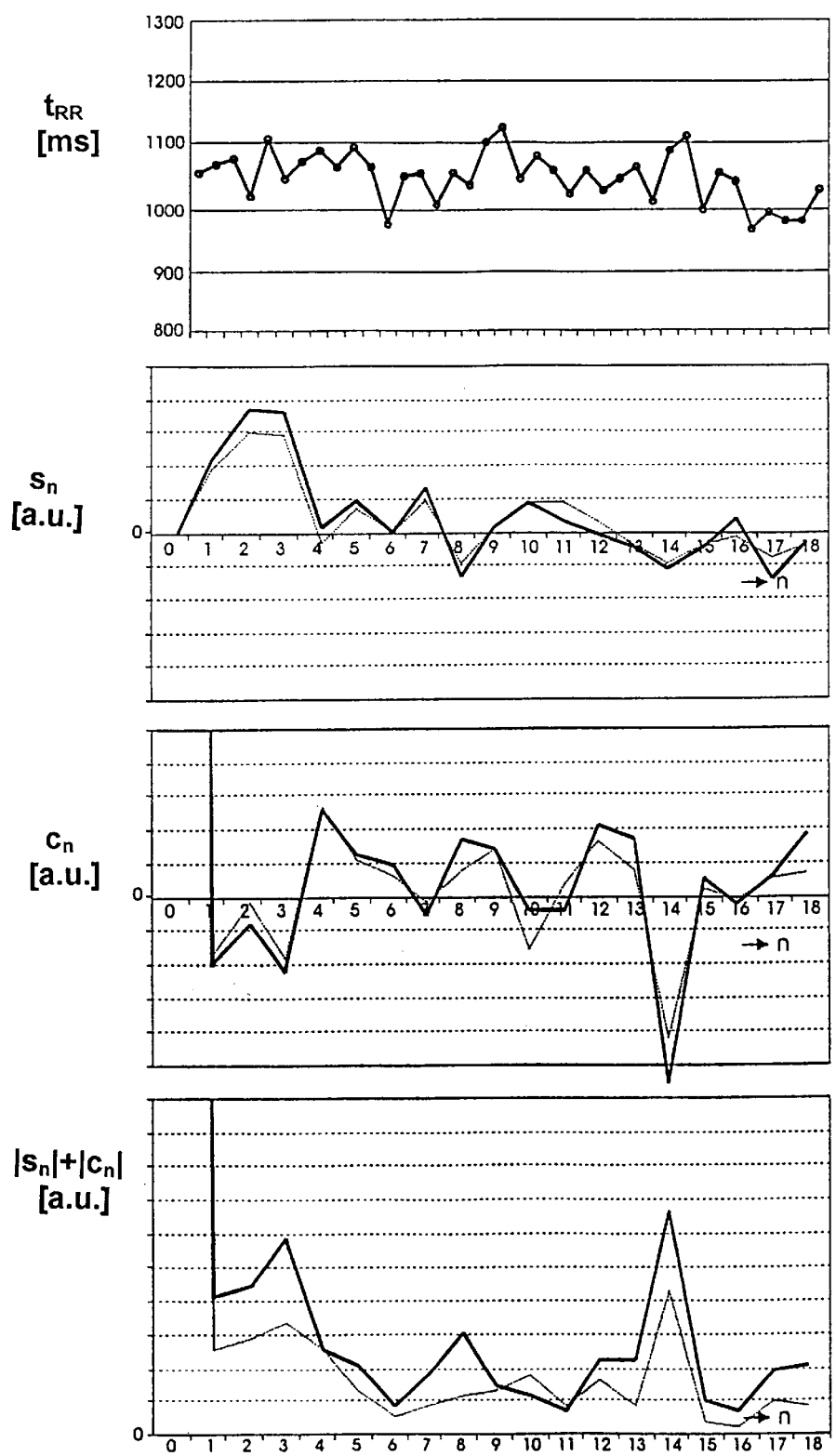
FIG. 4 shows a diagram of an RR interval course from an ECG section and the spectral components calculated using the fuzzy Fourier transformation approximation method plus frequency analysis.

FIG. 4 shows the evaluation results using the approximation method according to this invention in a concrete, practical example. The uppermost diagram in FIG. 4 shows a portion of the measurement of the RR intervals determined from an ECG signal by scanning at a scanning interval of 1.25 sec. It is obvious that the period duration of the RR intervals varies between approx. 970 and 1,130 ms.

When using the discrete Fourier transformation and the aforementioned approximation method, both calculation types result in maximum values at n=3 and n=14 as can be seen in the lower diagram of FIG. 4. These two maximum values represent frequencies of 0.075 Hz and 0.35 Hz, respectively.

Figure 5:
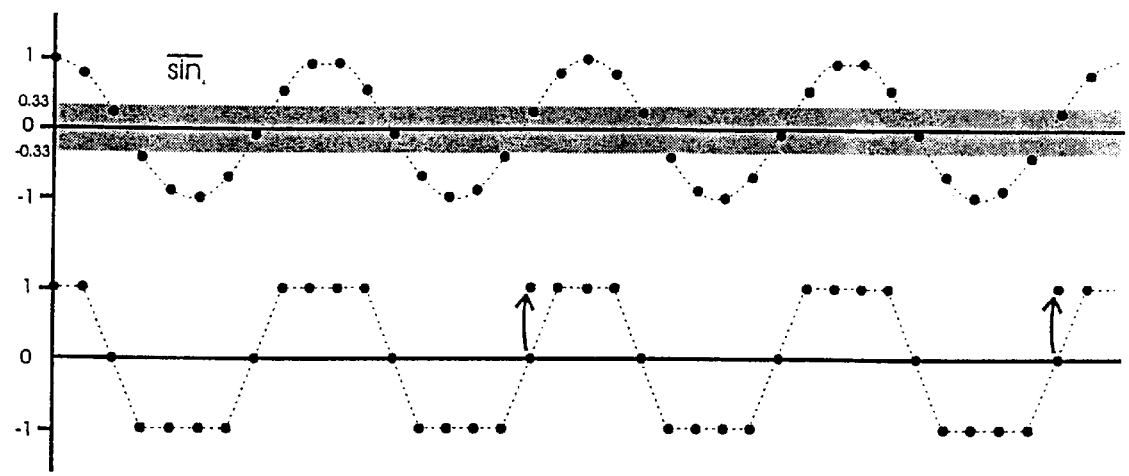
FIG. 5 shows a diagram similar to FIG. 1 with corrected approximate vector values.

During the use of the approximation method, it was also found that the condition applicable to the discrete Fourier transformation requiring that the sum of the components of a single eigenvector (except the vector $\cos_0$) equals 0 is not met by some approximations of the cosinus eigenvectors. A sum of −2 or 2 was obtained as shown as a dashed line of the approximate vector values in the lower diagram of FIG. 5. This would result in a very low-frequent peak in the calculated frequency spectrum. To avoid this, the approximate vector values are corrected so that the sum value equals 0. In the example shown in FIG. 5, two approximate values equalling 0 are raised to be +1 as indicated by the two arrows. This correction results in a sum of 0 of the approximate vector values.

Finally, it should be noted that the vector length 2N has a significant influence on the accuracy of the fuzzy Fourier transformation. If it is possible to split the length N into a plurality of smaller vectors of an equal length 1, so that N=n·1 applies, similar approximations occur several times during the transformation of the eigenvectors. In certain frequencies, this may produce considerable secondary maximum values up to 30% in the calculated frequency spectre A(f). So the optimum vector length is one in which the length N corresponds to a prime number, i.e.

$$2N = 2 \cdot \text{prime number.}$$

In the examples described above, the value of 2N=2·19=38.

The following tables 1 and 2 show suitable approximate vector values for the own vectors $\sin_{n,i}$ and $\cos_{n,i}$.

What is claimed is:

1. A method of calculating the heart rate variability of the human heart to be used in an ECG monitor, said method comprising the steps of:

scanning an ECG signal received from the ECG monitor during a scanning interval, determining from the scanned ECG signals a number of discrete measuring values representative of the heart rate variability, and evaluating these discrete measuring values on the basis of a Fourier transformation, wherein a frequency spectrum of the measuring values is calculated from Fourier coefficients of the Fourier transformation, which are calculated from a combination of said measuring values with sinus- and cosinus-shaped Fourier vectors of the Fourier transformation wherein the Fourier vectors involved in the calculation are a number of discrete real numerical vector values, and replacing the numerical vector values for calculating the frequency spectrum of the scanned measuring values by rough, integral approximate vector values of a limited number which roughly reproduce the Fourier vectors.

2. A method according to claim 1, wherein a maximum of 5 numerical values symmetrically surrounding the value zero are used as rough approximate values for said Fourier vectors.

3. A method according to claim 2, wherein −1, 0, and +1 are used as approximate values for the Fourier vectors.

4. A method according to claim 3, wherein said approximate values are made dependent from the actual numerical vector values as follows:

−0.33<numerical vector value<+0.33: approximate value=0 numerical vector value<−0.33: approximate value =−1 numerical vector value>+0.33: approximate value=+1.

5. A method according to claim 4, wherein the assignment of the approximate values to the actual numerical vector values is stored as a table in said ECG monitor.

6. A method according to claim 4, wherein the approximate values are assigned by calculating those points in which the approximate vector values are changing.

7. A method according to claim 1, wherein the sum of the approximate vector values for each Fourier vector is formed and wherein in case of a deviation from the value 0 at least one approximate value is corrected in order to obtain a sum value of 0.

8. An ECG monitor comprising an operating program, wherein said operating program implements a calculation method according to claim 1.

9. An ECG monitor according to claim 8, wherein said ECG monitor is implantable into a human body.

10. An ECG monitor according to claim 8, wherein said ECG monitor is integrated into a pacemaker.

* * * * *